United States Patent [19]
Chang

[11] Patent Number: 5,221,283
[45] Date of Patent: Jun. 22, 1993

[54] APPARATUS AND METHOD FOR STEREOTACTIC SURGERY

[75] Inventor: Hsuan Chang, Clifton Park, N.Y.

[73] Assignee: General Electric Company, Schenectady, N.Y.

[21] Appl. No.: 883,741

[22] Filed: May 15, 1992

[51] Int. Cl.$^5$ .................. A61B 17/00; A61B 19/00
[52] U.S. Cl. ........................ 606/130; 606/1; 604/16
[58] Field of Search .............. 606/1, 96–98, 606/130; 128/653.1, 653.2, 653.5; 604/116

[56] References Cited

FOREIGN PATENT DOCUMENTS 1047472 10/1983 U.S.S.R. ................. 606/130
1342478 10/1987 U.S.S.R. ................. 606/130

OTHER PUBLICATIONS

"Tumor Stereotaxis", Patrick J. Kelly, M.D., 1991, pp. 1–50 (Chapter 1: Introduction and Historical Aspects) (Chapter 2: Stereotactic Instruments).
"Stereotactic Neurosurgery", Robert L. Galloway and Robert J. Maciunas, Critical Reviews in Biomedical Engineering, vol. 18, Issue 3, 1990, pp. 181–205.
"A New Computerized Tomographic-Aided Robotic Stereotaxis System", Y. S. Kwoh, Robotics Age, vol. 7, Issue 6, pp. 17–21, 1985.
"An Articulated Neurosurgical Navigation System Using MRI and CT Images", IEEE Trans. on Biomedical Engineering, Y. Kosugi et al., vol. 35, Issue 2, pp. 147–151, 1988.
Neurosurgery, (Edited by Wilkins and Rengachary), published by McGraw-Hill Book Company, pp. 2465–2489, copyright date 1985.

Primary Examiner—Stephen C. Pellegrino
Assistant Examiner—Glenn Dawson
Attorney, Agent, or Firm—Gene Bolmarcich; Paul R. Webb, II

[57] ABSTRACT

The trajectory of a surgical instrument or tool used for a stereotactic medical procedure is controlled by a passive apparatus having two pivots into which the tool may be inserted. The pivots, which serve as end effectors, are placed at points along a selected trajectory. The pivots are mounted to members attached to carriages. The carriages allow movement in a plane, whereas the members may move perpendicular to the plane. Indicia allow the pivots to be moved to a desired point and fasteners then secure the pivots in place, while allowing the pivots free rotation relative to two perpendicular axes.

17 Claims, 6 Drawing Sheets

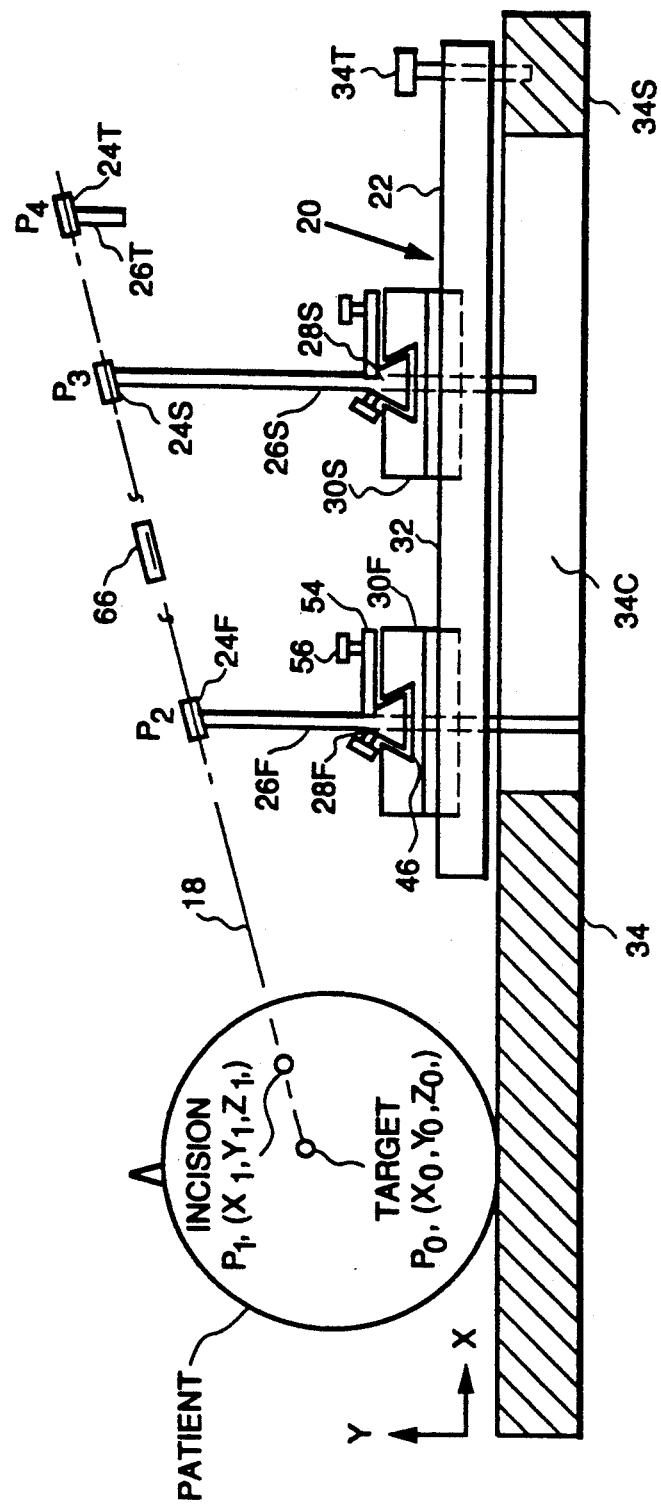
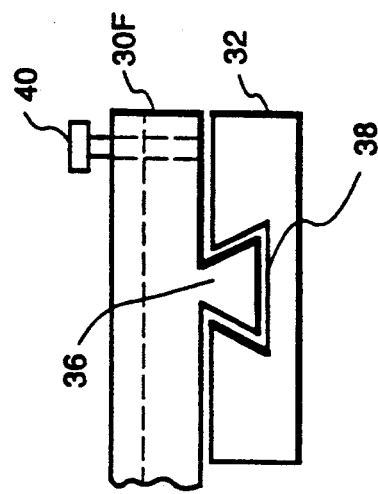
Fig. 5
Fig. 6

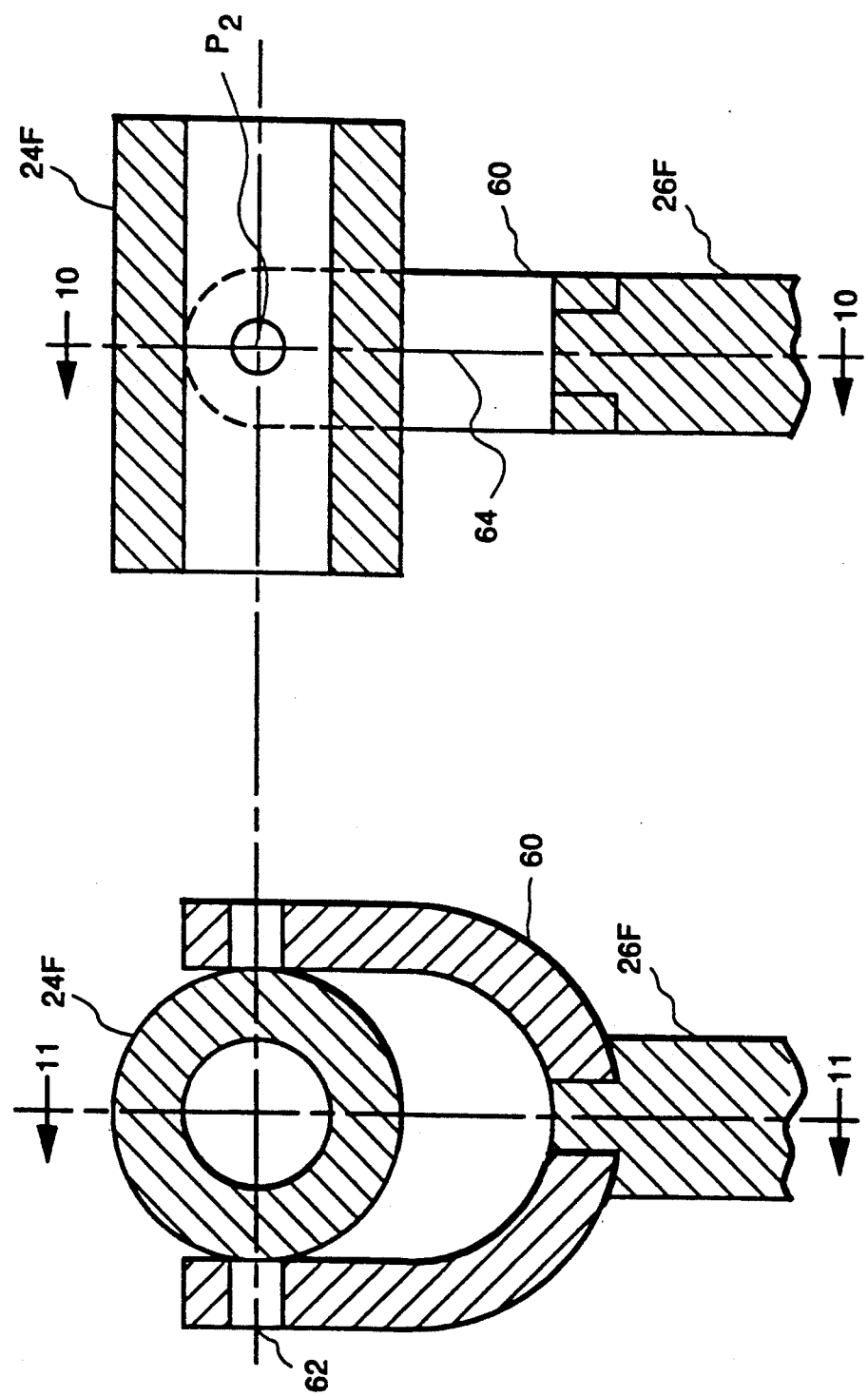

APPARATUS AND METHOD FOR STEREOTACTIC SURGERY

CROSS REFERENCE TO RELATED APPLICATION

This application relates to copending application Ser. No. 07/883,736 filed concurrently herewith and assigned to the same assignee as the present invention.

BACKGROUND OF THE INVENTION

This invention relates to a method and apparatus for trajectory support of a surgical tool during an imaging-guided surgical operation.

Stereotactic frames play an important part in stereotactic surgery. Such frames provide a means to define a mechanical or physical trajectory in three dimensions and to support a surgical instrument or tool such that it may reach a target along the trajectory. For example, a patient may have a brain tumor which should be removed or otherwise treated. An imaging system such as computerized tomography allows the surgeon to precisely define the location of the tumor or other target. The surgeon selects an incision point on the skull of the patient and the location of the incision point is relatively precisely identified. The trajectory which the surgical tool or instrument should use is defined by the target and incision. Various stereotactic frames have been used to insure that the surgical tool follows the planned trajectory.

Since much of the activity in stereotactic surgery has been related to neurosurgery, targets are usually considered points inside a sphere, whereas incision points are selected from the surface of the sphere. Accordingly, the frames have been designed to work in a partly enclosed space such as the human head. Setting up of such an apparatus usually involves setting a number of rotational angles. For example, the most popular BRW frame uses four angles. Given the target and incision points, a special program determines four angles. As shown in FIG. 1, the prior art BRW frame 10 allows placement of a needle 12 within a patient. The frame 10 supports the needle 12 in its trajectory. Because the frame uses a non-intuitive coordinate system, a surgeon often has to repeat the calculations several times to make sure that the set of angles are correct. Further, the calculations are non-linear and the non-linearity may introduce positional errors.

Since stereotactic surgery is usually much less invasive than normal surgery, it is becoming more popular for surgical operations beyond traditional stereotactic neurosurgery. The usefulness of stereotactic surgery for operating on the neck, spine, and abdomen is becoming more appreciated. In those operations, mechanical support without a frame becomes essential. Typically, a frameless support system would use a robotic arm. Given a target and incision pair based upon a preoperatively acquired three dimensional image set and a patient space to image space registration scheme, a robot arm can be programmed to provide a trajectory support for the surgical instrument.

FIG. 2 shows a prior art robotic arm arrangement developed by Kwoh. The idea is that the patient is imaged in the same reference system as the robot arm sits. Once the target and incision pair is determined, the computer that drives the arm can be instructed to orient an end effector 14 to such a position that a surgical tool can be held by the assembly and extended to touch the target inside the patient. The arm in this design is active which, when instructed, does the orientation itself. Furthermore, it can be instructed to aim the end effector at the target as the trajectory is being changed. This feature allows the surgeon to explore all the possible incision points. This arrangement is described in more detail in Y. S. Kwoh, "A New Computerized Tomographic-Aided Robotic Stereotaxis System", Robotics Age, 7(6):17-21(1985).

A prior art passive arm is shown in FIG. 3. This design allows the surgeon to move an end effector 6 around and, correspondingly, the position of the end effector is displayed in the context of the three dimensional image acquired preoperatively. This design enables the surgeon to explore possible trajectories with total freedom. More details about this design may be obtained from Y. Kosugi et al., "An Articulated Neurosurgical Navigation System Using MRI and CT Images", IEEE Transactions on Biomedical Engineering, 35(2):147-151(1988).

Among problems with robot assisted and other frameless support systems are design complexities. Such robotic designs often leave little control to the surgeon. Furthermore, the sophisticated and expensive positional feedback systems are unnecessary when one is within imaging-guided surgical procedures. That is the imaging process can be used to track the position of the instrument or tool such that calculations of such information indirectly from the positional information of all the joints of the robot arm is not required.

OBJECTS AND SUMMARY OF THE INVENTION

Accordingly, it is a primary object of the present invention to provide a new and improved stereotactic trajectory support apparatus and method.

A more specific object of the present invention is to provide stereotactic trajectory support using a relatively simple and inexpensive design.

A further object of the present invention is to provide stereotactic trajectory support which is relatively convenient and user-friendly.

A further object of the present invention is to provide stereotactic trajectory support without requiring use of a non-intuitive coordinate system and/or without requiring non-linear calculations.

The above and other objects of the present invention are realized by a stereotactic trajectory apparatus having a support structure and first and second surgical tool holders supported by the support structure. The surgical tool holders are independently movable relative to the support structure to positions corresponding to different x, y, z coordinates, the x, y, z coordinates corresponding respectively to orthogonal x, y, and z axes. The first and second surgical tool holders are respectively first and second pivots. Each pivot defines a point on a surgical tool trajectory. Each pivot is rotatable about perpendicular first and second pivot axes without changing the x, y, z coordinates of the corresponding point. The first pivot axis of each pivot is perpendicular to an xz plane in which the x and z axes extend and the second pivot axis of each pivot is parallel to the xz plane.

First and second members are movably attached respectively to corresponding first and second carriages. Each carriage is supported by the support structure for movement in a plane perpendicular to a lengthwise direction of the corresponding member. The first and second members extend lengthwise in parallel and the first and second carriages are mounted for movement in tracks on the support structure.

The support structure further includes parallel first and second carriages tracks extending along the z axis in which the first and second carriages move and each of the first and second carriage tracks is movable along the x axis. The support structure further includes an x track extending along the x axis and in which each of the first and second carriage tracks is movable. Fasteners allow selective fixing of the first and second carriages respectively to the first and second carriage tracks. Other fasteners allow selective fixing of the first and second carriage tracks to the x track. Still further fasteners allow selective fixing of the first and second members respectively to the first and second carriages. Indicia indicative of the x, y, z coordinates of the points defined by the first and second pivots are located on the support structure and/or the members.

Each of the pivots is always freely movable about its first and second pivot axes unless a surgical tool is disposed within the pivot. In other words, the trajectory apparatus does not have any means for locking the pivots against movement in their first and second pivot axes.

Advantageously, the apparatus is passive.

The method of the present invention includes identifying a target $P_0$ and incision pint $P_1$ for performing a medical stereotactic procedure. A trajectory path having $P_0$ and $P_1$ thereon is determined for a surgical tool. Independently movable first and second pivots are secured respectively at points $P_2$ and $P_3$ on the trajectory path. Points $P_2$ and $P_3$ are determined by positioning the first and second pivots using indicia linearly related to x, y, z coordinates corresponding to orthogonal x, y, z axes. Each of the first and second pivots is rotatable about perpendicular first and second pivot axes without changing the x, y, z coordinates of the corresponding respective one of points $P_2$ and $P_3$. Next, a surgical tool is placed through the first and second pivots to extend along the trajectory path to within the patient.

Before the securing step, first and second carriages are moved to positions corresponding to the x, z coordinates respectively of $P_2$ and $P_3$, and first and second members, which are movably mounted respectively to the first and second carriages, are moved to locations such that first and second pivots mounted respectively thereon are at the y coordinates respectively of $P_2$ and $P_3$. The first and second carriages moved in an xz plane in which the x axis and z axis are disposed by movement along tracks. The securing step includes securing the first and second carriages and securing the first and second members.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 5 is an end view of a structure used to implement the concept of FIG. 4;

FIG. 6 is a view of a part of FIG. 5 from the side;

FIG. 10 is cross section view of a pivot;

FIG. 11 is a cross section view taken along lines 11—11 of FIG. 10 and including lines 10—10 corresponding to the view of FIG. 10.

DETAILED DESCRIPTION

Figure 1:
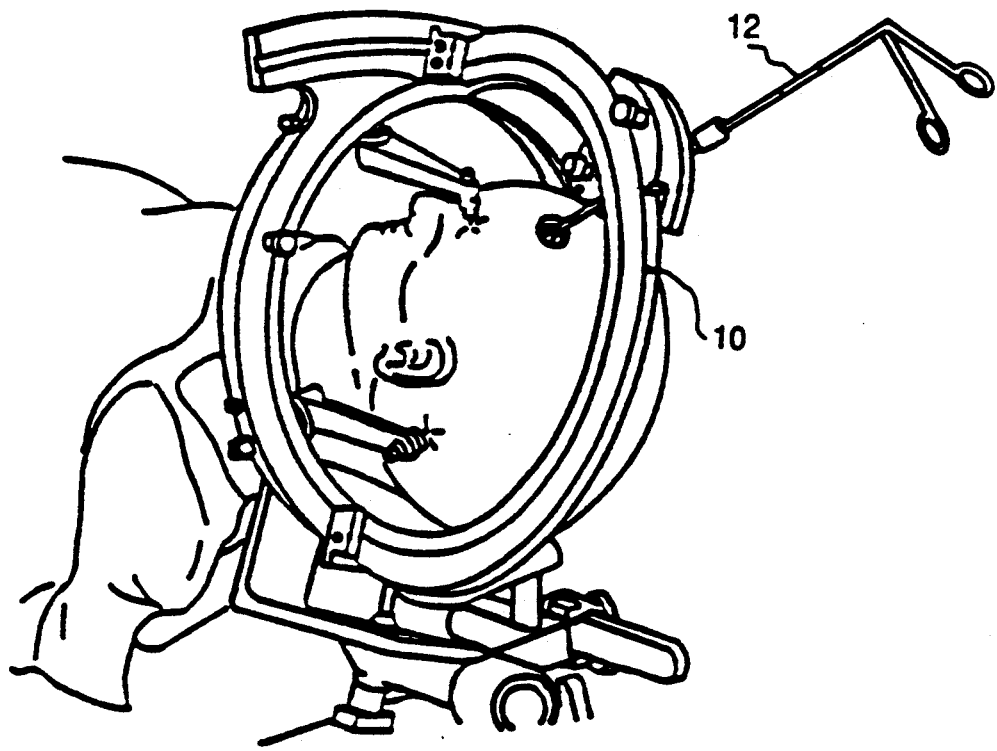
FIG. 1 is a simplified perspective view of a patient having a prior art stereotactic frame attached to him as discussed above.
Figure 2:
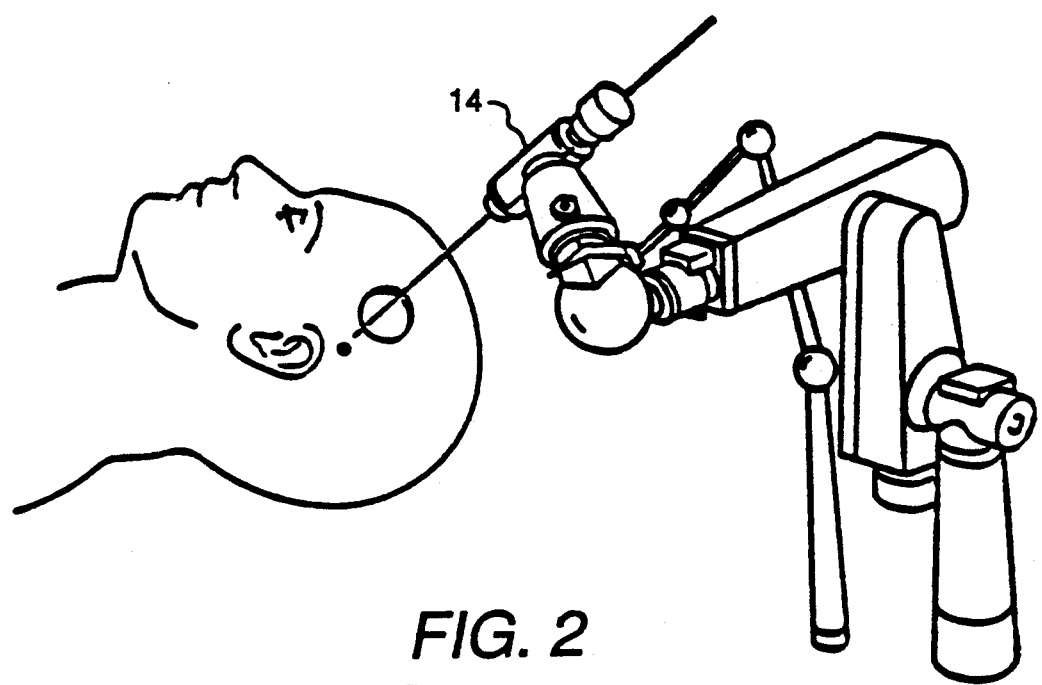
FIG. 2 shows a perspective of a patient having surgery using a prior art robotic arm as discussed above.
Figure 3:
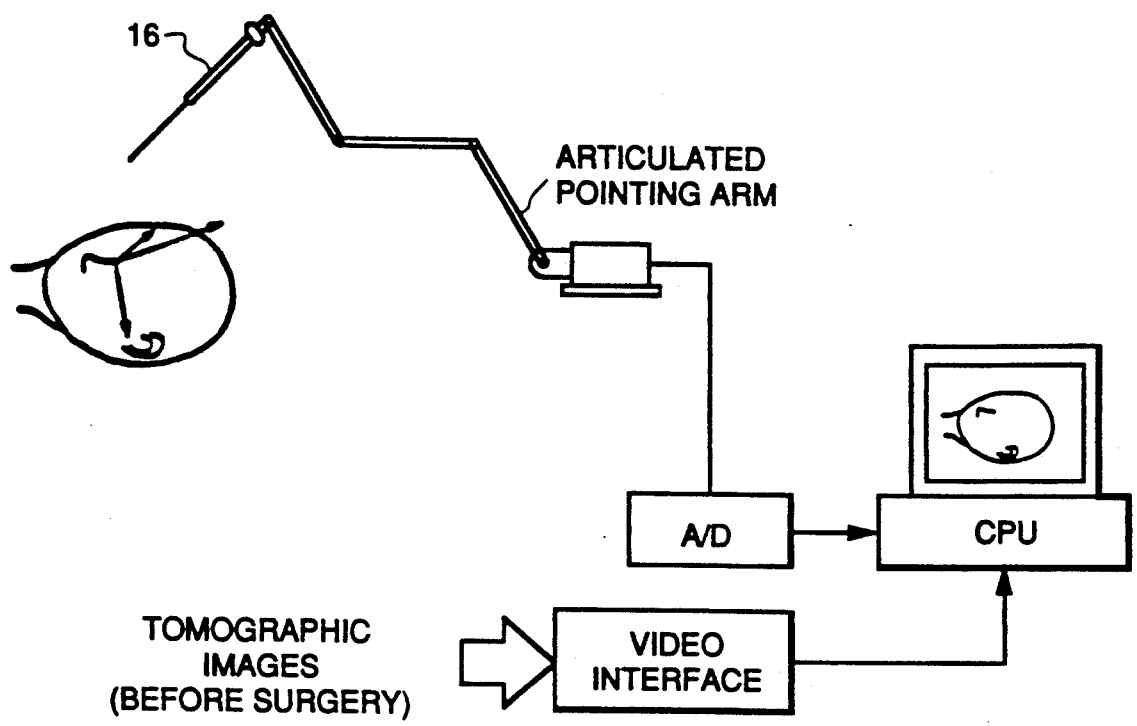
FIG. 3 shows a prior art passive arm system for operating on a patient as discussed above.

The principle of the operation of the present invention will be discussed with reference to FIG. 4 in which points $P_0$ and $P_1$ respectively are the target and incision point within a patient. The target and incision point would be determined using known techniques as discussed above. Specifically, an imaging system allows the surgeon to select the target $P_0$ which has coordinates $(X_0, Y_0, Z_0)$. The incision point $P_1$ having coordinates $(X_1, Y_1, Z_1)$ is selected so that the two points $P_0$ and $P_1$ define a trajectory 18. For the usual case in which the trajectory 18 is a line, the line can be written as:

$$x = \frac{a}{b}(y - Y_0) + X_0 \quad (1)$$

$$z = \frac{c}{b}(y - Y_0) + Z_0 \quad (2)$$

where $a = X_1 - X_0$, $b = Y_1 - Y_0$, and $c = Z_1 - Z_0$. Using the two equations, two points $P_2 = (X_2, Y_2, Z_2)$ and $P_3 = (X_3, Y_3, Z_3)$ can be selected which lie on the same trajectory line 18 defined by points $P_0$ and $P_1$. A typical way to make the selection would be to pick two heights $Y_2$ and $Y_3$ and then use the equations 1 and 2 to calculate the X and Z values for those points. Once the coordinates for the points $P_2$ and $P_3$ are determined, apparatus 20 of the present invention would be used. Specifically, the apparatus 20 is a stereotactic trajectory apparatus having a support structure 22 having first and second pivots 24F and 24S respectively supported thereby. As will be discussed in more detail below, the pivots 24F and 24S may be sleeves, rings, or other shapes adapted to receive a surgical tool, such as a needle, such that two of the pivots made together hold the needle along a trajectory path such as the line 18. The first and second pivots are respectively mounted to first and second members 26F and 26S, which is turn are secured in respective first and second carriages 28F and 28S. Carriages 28F and 28S move along support structure 22 in the xz plane. More specifically, carriages 28F and 28S travel along corresponding first and second z tracks 30F and 30S. The tracks 30F and 30S move in the x direction by track movement along two parallel x tracks 32.

Figure 4:
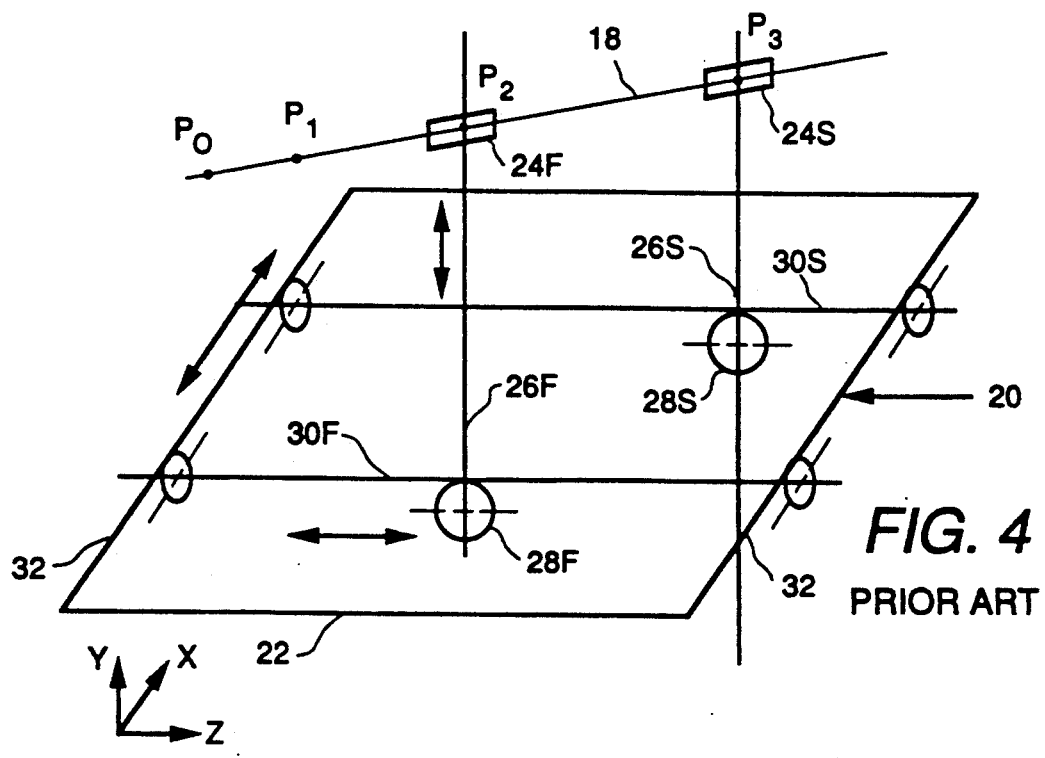
FIG. 4 is a simplified perspective illustration of the concept of the present invention.

Although not shown in the schematic of FIG. 4, indicia would be included on the support structure 22 and the members 26F and 26S so that the pivots 24F and 24S could be precisely placed at points $P_2$ and $P_3$. Additionally, indicia may be included on the surgical tool, such as needle (not shown) which would be inserted in pivot 24S and along trajectory line 18 so that, by knowing the distance from $P_3$ to $P_0$, the surgeon can insert the needle or other tool within pivot 24S only as far as necessary so that the tip of the needle would reach $P_0$.

Turning now to FIG. 5, the trajectory apparatus 20 of the present invention is shown attached to an operating table 34 upon which a patient is secured. The apparatus 20 is shown secured to portion 34S of table 34 by a thumb screw 34T at one corner of the base 22 of apparatus 20. However, in actual practice, four such thumb screws or other fasteners may be used at each of four corners of the generally rectangular base 22. Each of the thumb screws would extend through a hole in part of the base 22 and into corresponding holes in parts of the table 34. More specifically, the thumb screws could extend through holes in the two identical x tracks 32 (only one of which is visible in FIG. 5). The table 34 includes a cut-out portion 34C, which may be a rectangular cut-out section corresponding in shape to the base 22 and being slightly smaller in size than the base 22. The cutout section allows members 26F and 26S to be moved vertically (i.e., along the y axis) relative to their respective first and second carriages 28F and 28S.

Continuing to view FIG. 5, but also considering FIG. 6, it will be seen that the track 30F moves along opposite side tracks 32 (only one is visible in FIGS. 5 and 6) by use of a wedge portion 36 sliding in a mating channel or slot 38. An arrangement such as thumb screw 40 extending through a hole in track 30F and pressing against the top surface of track 32 or some other fastener arrangement may be used to secure track 30F relative to track 32, while still allowing movement of track 30F relative to track 32 when such movement is desired in order to place pivot 24F in its proper position. Although only one end of the track 30F is shown in FIG. 6, it will be appreciated that the opposite end of the track 30F would be constructed in identical fashion and would slide in the other track 32.

Figure 7:
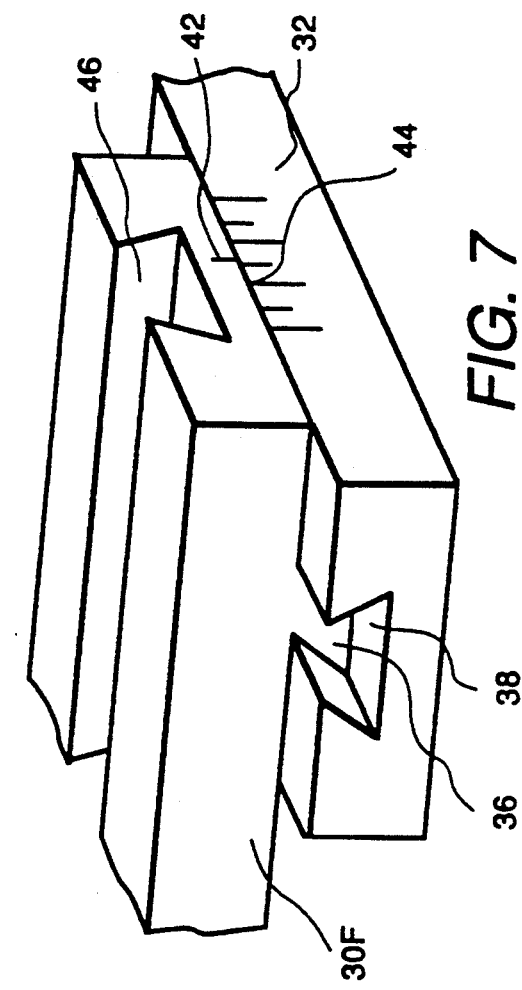
FIG. 7 is a perspective view of a part of the structure of FIG. 5.

With reference now to FIG. 7, the track 30F may have a mark 42 disposed on its end, which mark lines up with different indicia 44 on track 32, the indicia 44 having numerals (not shown) such that the x coordinate of the pivot 24F may be read from the indicia 44.

Figure 9:
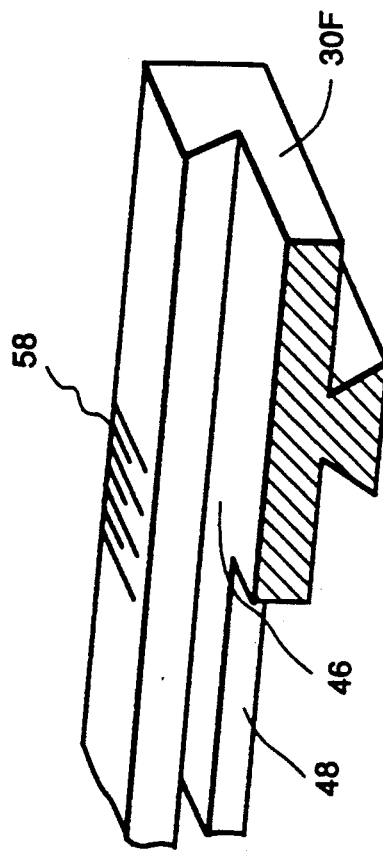
FIG. 9 is a perspective view with parts broken away and a portion in cross section of a part of the FIG. 5 structure.
Figure 8:
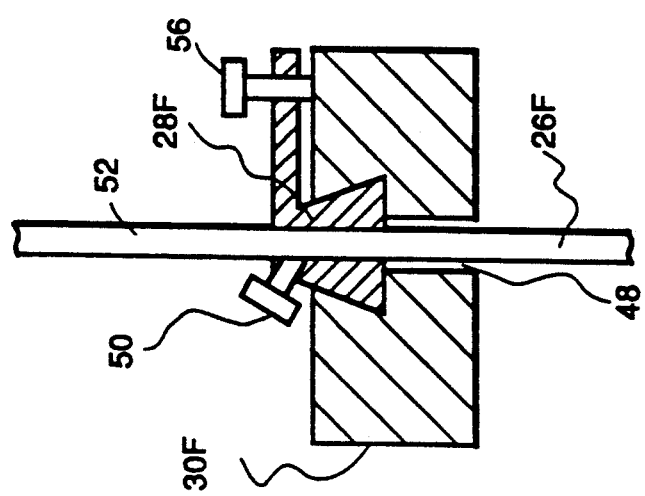
FIG. 8 is a cross section view of a part of the structure of FIG. 5.

With reference now to FIGS. 7-9, the track 30F has a wedge-shaped channel 46 in which the carriage 28F may slide. The bottom of channel 46 in which the carriage 28F may slide, has a cut-out slot 48 extending substantially along the length of channel 46 so that the member 26F may extend through a hole (not separately labeled) in carriage 28F. The member 26F is moved up and down so that the pivot 24F is disposed at the proper y coordinate whereupon a thumb screw 50 is used to fix it in position relative to carriage 28F. The thumb screw 50 may, as with the other thumb screws discussed herein, be replaced by other fastener elements.

Indicia 52 on member 26F may be read (as by lining up to the top of carriage 28F) to determine the y coordinate of the pivot 24F. As with the other indicia discussed, indicia 52 may have numbers (not shown) associated with indication marks and would extend substantially completely over the range of relative movement even though only a few indicia are shown in the figures.

The carriage 28F may have a flange 54 so that thumbscrew 56 (FIGS. 5 and 8) may lock the carriage against movement in the same fashion as discussed with respect to thumbscrew 40.

Indicia 58 (FIG. 8 only) are disposed on the top of track 30F to allow carriage 28F to be placed such that pivot 24F has the proper z coordinate. As with the other indicia, a marker, pointer, or part of the carriage 28F may line up with the indicia to allow reading thereof.

The member 26S, carriage 28S, and carriage (i.e., carriage accommodating) track 30S are respectively identical to member 26F, carriage 28F, and track 30F.

The arrangement of FIG. 5 gives the pivots 4F and 24S three degrees of freedom corresponding to the x, y, and z axes, which are three orthogonal axes. As used herein, the x, y, and z axes would not necessarily have the shown orientation with x anc z axes being horizontal and the y axis being vertical. Although the support structure 22 made of tracks 30F, 30S, and 32 is shown horizontal, attached to the table 34, and beside the patient in FIG. 5, other orientations and mounting arrangements might be used. The structure 22 could be suspended from the ceiling of the operating room with the pivots 24F and 24S disposed below the structure 22. The apparatus 20 might alternately be mounted so that structure 22 was vertical and members 26F and 26S extended horizontally. Regardless of the orientation and placement of the trajectory apparatus 20, the indicia on the apparatus should give coordinates relative to the patient frame of reference, either directly or by use of a simple linear transformation.

Turning now to FIGS. 10 and 11, the construction of pivot 24F will be discussed. (Pivot 24S is identical to pivot 24F.) Pivot 24F is shown as a sleeve, although it could alternately be a ring, loop, partial ring, or other shape allowing it to receive a surgical tool, such as a needle, directly or indirectly (e.g., needle holder or cannula fits in pivot and in turn holds needle within pivot). Pivot 24F is mounted to yoke 60 for pivoting about pivot axis 62. Yoke 60 is in turn mounted to member 26F for rotation about pivot axis 64.

Once the pivots 24F and 24S are placed at points $P_2$ and $P_3$, the surgeon passes the tip of a surgical tool 66 (partially shown only in FIG. 5) through pivot 24S and towards pivot 24F. The pivots 24F and 24S are end effectors which orient themselves by assuming the proper angles (i.e., no need to set an angle explicitly) by pivoting about their two pivot axes as the tool 66 goes into pivot 24F. The tool will be constrained to follow trajectory path 18 and the surgeon would insert it to the previously determined depth so that the tip of tool 66 reaches the target.

As a check on the linear calculations (i.e., equations 1 and 2 above) and the settings actually used for placement of pivots 24F and 24S, a third pivot 24T and third member 26T (FIG. 5 only) might be placed at a point $P_4$ by applying the techniques used for the other pivots. If there was a calculation mistake or mistake in positioning the three pivots, the identical pivots 24F, 24S, and 24T would not line up and would prevent the tool 66 from being applied to the patient. The member 26T is only partially shown in FIG. 5 and would be securable to a carriage and track (not shown) in the same fashion as member 26F.

Al alternate way of checking the settings on apparatus 20 would involve using a phantom to establish simulated target and incision points as described in the above mentioned present inventor's U.S. application Ser. No. 07/883,736 (RD-21255), filed concurrently herewith, entitled "METHOD AND APPARATUS FOR STEREOTACTIC TRAJECTORY SPECIFICATION", assigned to the assignee of the present application and hereby incorporated by reference. That application uses a phantom which is similar to some respects to apparatus 20.

The apparatus 20, or parts of it, may be made of non-ferromagnetic materials such as carbon fiber for applications in magnetic resonance imaging-guided surgeries.

Figure 12:
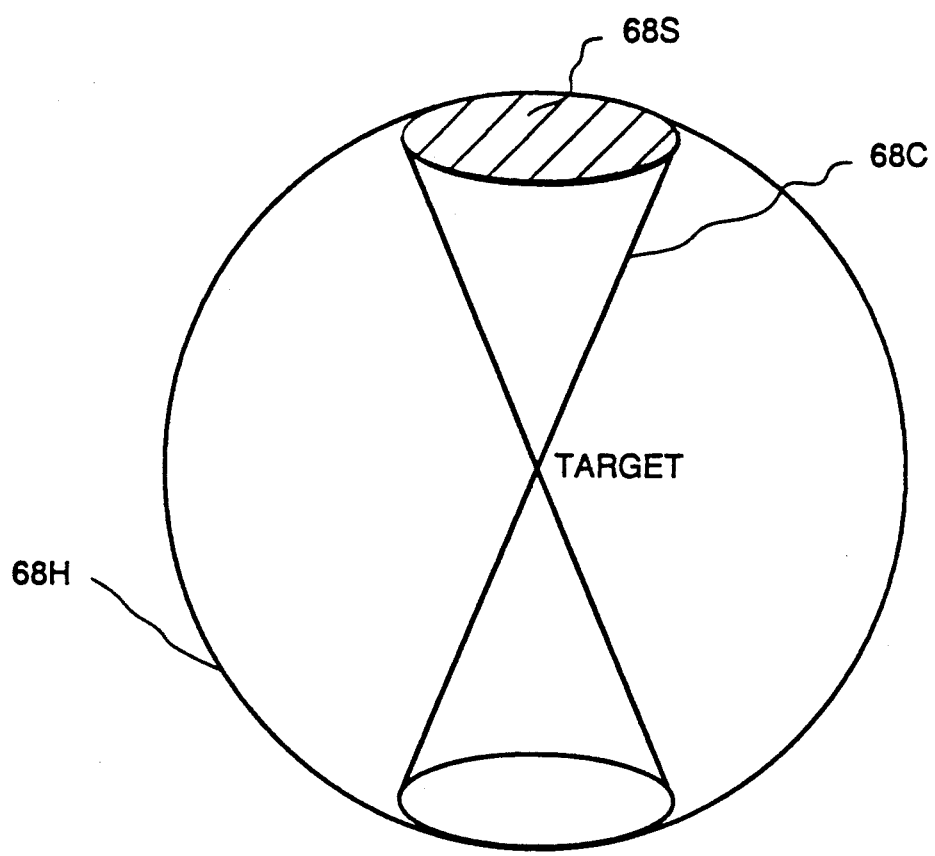
FIG. 12 is a graphic illustrating a range of trajectories.

FIG. 12 shows the head 68H of a patient to illustrate that trajectories within cones 68C corresponding to incision points at surface area 68S could not be used with the present invention as carriages 28F and 28S could not be disposed at the same or too close x coordinates. The size of the cones could be minimized by making tracks 30F and 30S as narrow as possible or otherwise optimizing the design of the tracks and/or the pivots. In ordinary situations, the patient can be repositioned if the proposed trajectory falls within one of the cones. If desired, the tracks 30F and 30S could be mounted to slide in different, vertically offset x tracks so as to improve the range of allowable trajectories.

Although various specific constructions have been described herein, it is to be understood that these are for illustrative purposes only. Various modifications and adaptations will be apparent to those of skill in the art. Accordingly, the scope of the present invention should be determined by reference to the claims appended hereto.

What is claimed is:

1. A stereotactic trajectory apparatus comprising:
   a support structure; and
   first and second surgical tool holders supported by said support structure and independently movable relative to said support structure to positions corresponding to different x, y, z coordinates, the x, y, z coordinates corresponding respectively to orthogonal x, y, and z axes, wherein said first and second surgical tool holders are respectively first and second pivots, each pivot defining a point on a surgical tool trajectory, and wherein each pivot is rotatable about perpendicular first and second pivot axes without changing the x, y, z coordinates of the corresponding point.

2. The stereotactic trajectory apparatus of claim 1 wherein said first pivot axis of each pivot is perpendicular to an xz plane in which the x and z axes extend and said second pivot axis of each pivot is parallel to the xz plane.

3. The stereotactic trajectory apparatus of claim 2 further comprising first and second members each having top and bottom portions, said members being movably attached respectively to corresponding first and second carriages at their bottom portions, and to said first and second surgical tool holders at their top portions, each carriage being supported by the support structure for movement in a plane perpendicular to the lengthwise direction of the corresponding member.

4. The stereotactic trajectory apparatus of claim 3 wherein said first and second members extend lengthwise in parallel and said first and second carriages are mounted for movement in tracks on said support structure.

5. The stereotactic trajectory apparatus of claim 4 wherein said tracks of said support structure further comprises parallel first and second carriage tracks extending along the z axis in which said first and second carriages move and each of said first and second carriage tracks is movable along the x axis.

6. The stereotactic trajectory apparatus of claim 5 wherein said tracks of said further comprises an x track extending along the x axis and in which each of said first and second carriage tracks is movable.

7. The stereotactic trajectory apparatus of claim 6 wherein said support structure further comprises fasteners for selectively fixing said first and second carriages respectively to said first and second carriage tracks, fasteners for selectively fixing said first and second carriage tracks to said x track, and fasteners for selectively fixing said first and second members respectively to said first and second carriages.

8. The stereotactic trajectory apparatus of claim 7 further comprising indicia of said support structure indicative of the x, y, z coordinates of said points defined by said first and second pivots.

9. The stereotactic trajectory apparatus of claim 5 wherein each of said pivots is always freely movably about its first and second pivot axes unless a surgical tool is disposed within the pivot.

10. The stereotactic trajectory apparatus of claim 1 wherein each of said pivots is always freely movably about its first and second pivot axes unless a surgical tool is disposed within the pivot.

11. The stereotactic trajectory apparatus of claim 1 further comprising indicia on said support structure the x, y, z coordinates of said points defined by said first and second pivots.

12. The stereotactic trajectory apparatus of claim 1 further comprising a third surgical tool holder supported by said support structure and movable independently of said first and second surgical tool holders to positions corresponding to different x, y, z coordinates, and wherein said third surgical tool holder is a third pivot defining a point on a surgical tool trajectory and is rotatable about perpendicular first and second pivot axes without changing the x, y, z coordinates of the corresponding points.

13. A method comprising the steps of:
    identifying a target $P_0$ and incision point $P_1$ for performing a medical stereotactic procedure;
    determining a trajectory having $P_0$ and $P_1$ thereon for a surgical tool;
    securing independently movable first and second pivots respectively at points $P_2$ and $P_3$ on the trajectory, points $P_2$ and $P_3$ determined by positioning the first and second pivots using indicia linearly related to x, y, z coordinates corresponding to orthogonal x, y, z axes, each of the first and second pivots being rotatable about perpendicular first and second pivot axes without changing the x, y, z coordinates of the corresponding respective one of points $P_2$ and $P_3$; and
    placing a surgical tool through the first and second pivots to extend along the trajectory to within the patient.

14. The method of claim 13 further comprising the steps of, before the securing step:
    moving first and second carriages to positions corresponding to the x, z coordinates respectively of $P_2$ and $P_3$; and
    moving first and second members movably mounted respectively to said first and second carriages to locations such that the first and second pivots mounted respectively thereon are at the y coordinates respectively of $P_2$ and $P_3$.

15. The method of claim 14, wherein the first and second carriages are moved in an xz plane, in which the x and z axes are disposed, by movement along tracks.

16. The method of claim 14 wherein the securing step includes securing the first and second carriages and securing the first and second members.

17. The method of claim 13 further comprising: securing an independently movable third pivot at point $P_4$ on the trajectory, point $P_4$ determined by positioning the third pivot using the indicia, the third pivot being rotatable about perpendicular first and second pivot axes associated with the third pivot and without changing the x, y, z coordinates of point $P_4$; and placing a surgical tool through the third pivot, as well as the first and second pivots, to extend along the trajectory to within the patient.

* * * * *

UNITED STATES PATENT AND TRADEMARK OFFICE
CERTIFICATE OF CORRECTION

PATENT NO. : 5,221,283
DATED : June 22, 1993
INVENTOR(S) : Hsuan Chang

It is certified that error appears in the above-indentified patent and that said Letters Patent is hereby corrected as shown below:

In the Drawings, Fig. 4, delete the phrase "PRIOR ART".

Signed and Sealed this

Twenty-second Day of February, 1994

Attest:

BRUCE LEHMAN

Attesting Officer

Commissioner of Patents and Trademarks